United States Patent [19]

Bosse et al.

[11] Patent Number: 4,464,457
[45] Date of Patent: Aug. 7, 1984

[54] 10-PHENYL-1,3,9-TRIAZAANTHRACENES AND PHOTOPOLYMERIZABLE MIXTURE CONTAINING SAME

[75] Inventors: Dieter Bosse, Hofheim; Rainer Wingen, Frankfurt; Klaus Horn, Hofheim; Walter Lutz, Mainz-Kastel, all of Fed. Rep. of Germany

[73] Assignee: Hoechst Aktiengesellschaft, Frankfurt am Main, Fed. Rep. of Germany

[21] Appl. No.: 527,466

[22] Filed: Aug. 29, 1983

[30] Foreign Application Priority Data

Sep. 2, 1982 [DE] Fed. Rep. of Germany ....... 3232620

[51] Int. Cl.$^3$ .................. C07D 471/04; C08F 2/46; G03C 1/70
[52] U.S. Cl. ................... 430/288; 544/249; 544/250; 204/159.16; 204/159.23; 430/916; 430/920; 430/910
[58] Field of Search ............ 544/249, 250, 279; 252/600; 204/159.16, 159.18, 159.23; 430/288, 915, 916, 920, 910

[56] References Cited

U.S. PATENT DOCUMENTS

| | | | |
|---|---|---|---|
| 3,765,898 | 10/1973 | Bauer et al. | 96/115 P |
| 3,959,100 | 5/1976 | McGinniss | 204/159.15 |
| 4,011,324 | 3/1977 | Althuis | 424/251 |
| 4,277,603 | 7/1981 | Tolman et al. | 544/250 |
| 4,296,196 | 10/1981 | Faust | 430/271 |

FOREIGN PATENT DOCUMENTS 1354541  5/1974  United Kingdom .

OTHER PUBLICATIONS

E. Campaigne and G. Randau, "An Unusual Arylation of 4–Oxo–3,4–Dihydropyrimido[4,5-b]Quinoline (1)", *Journal of Heterocyclic Chemistry*, vol. 8, No. 1, 1971, pp. 111–120.
C. V. Wilson, "Azaanthracenes", Chapter I of *Six--Membered Heterocyclic Nitrogen Compounds with Three Condensed Rings*, by C. F. H. Allen, part of *The Chemistry of Heterocyclic Compounds*, Monograph Series, Interscience Publishers, Inc., New York, 1958, pp. 119–122.
Darrell E. O'Brien et al., "Synthesis of 10–Deazariboflavin and Related 2,4–Dioxopyrimido[4,5-b]-Quinolines(1a)," J. of Heterocyclic Chem., pp. 99–105, (1970).

*Primary Examiner*—John E. Kittle
*Assistant Examiner*—Cynthia Hamilton
*Attorney, Agent, or Firm*—Schwartz, Jeffery, Schwaab, Mack, Blumenthal & Koch

[57] ABSTRACT

The present invention relates to novel 10-phenyl-1,3,9-triazaanthracenes and to a photopolymerizable mixture which contains, as the essential components,
 (a) a polymeric binder
 (b) a polymerizable compound having at least two terminal, ethylenically unsaturated groups and a boiling point of more than 100° C., and
 (c) a 10-phenyl-1,3,9-triazaanthracene as the photoinitiator.

18 Claims, No Drawings

10-PHENYL-1,3,9-TRIAZAANTHRACENES AND PHOTOPOLYMERIZABLE MIXTURE CONTAINING SAME

BACKGROUND OF THE INVENTION

The present invention relates to novel 10-phenyl-1,3,9-triazaanthracenes and to a photopolymerizable mixture which contains, as the essential components,
(a) a polymeric binder
(b) a polymerizable compound having at least two terminal, ethylenically unsaturated groups and a boiling point of more than 100° C., and
(c) a 10-phenyl-1,3,9-triazaanthracene as the photoinitiator.

Photopolymerizable mixtures which contain the components (a) and (b) and a polynuclear heterocyclic compound as the photoinitator are known.

In German Pat. No. 20 27 467 (equivalent to British patent specification No. 1,354,541), specific derivatives of acridine and phenazine are described as initiators.

German Pat. No. 20 39 861 (equivalent to U.S. Pat. No. 3,765,898) discloses similar mixtures containing quinoxaline derivatives or quinazoline derivatives as initiators.

All these compounds act as excellent initiators when they are irradiated with actinic light, particularly from light sources emitting in the near ultraviolet range. But in recent times, metal halide-doped gas discharge lamps have become more and more commonly used for copying purposes because of their high luminous efficiency. Since these lamps have stronger emission values in the border range of the visible light, i.e., at about 400 nm and higher, than the hitherto conventionally used light sources, such as, for example, mercury vapor lamps, the absorption values of the known, highly efficient initiators are no longer optimally matched to the emissions of these light sources. Moreover, the variations possible by substitution of the known heterocyclic initiators are limited, i.e., by means of known production processes it is possible to modify other properties, such as solubility in aqueous or organic solvents or compatibility with various photopolymerizable mixtures, to only a limited degree by a purposeful synthesis.

SUMMARY OF THE INVENTION

Therefore, it is an object of the present invention to provide novel photoinitiators which possess a high efficiency similar to known photoinitiators, but which have light absorption values which extend more deeply into the short-wave visible range, and to which specific substituents can be purposefully attached in the course of their synthesis, which substituents impart various, desired properties to the final products, such as solubility and compatibility with other components.

It is also an object of the present invention to provide improved photopolymerizable compositions containing the novel photoinitiators according to the invention.

In accordance with one aspect of the present invention, there has been provided a photopolymerizable mixture consisting essentially of:
(a) a polymeric binder
(b) a polymerizable compound having at least two terminal, ethylenically unsaturated groups and a boiling point of more than 100° C., and
(c) a polynuclear N-heterocyclic compound as photoinitiator.

The mixture of the invention is characterized in that the N-heterocyclic compound corresponds to the general formula (A)

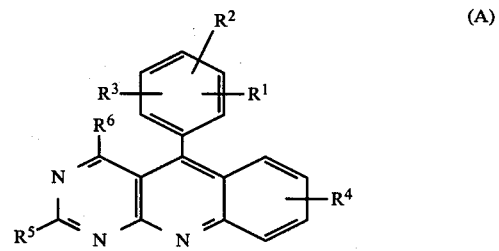

wherein
$R^1$, $R^2$ and $R^3$ are identical or different and each denotes a hydrogen or halogen atom, an alkyl or alkoxy group or a condensed aromatic radical
$R^4$ is a hydrogen or halogen atom, an alkyl, alkoxy, halogenoalkyl, alkylcarbonyl, alkoxycarbonyl or dialkylamino group or a condensed aromatic radical, and
$R^5$ and $R^6$ are identical or different and each denotes hydroxy, alkoxy or dialkylamino groups.

In accordance with another aspect of this invention, there are further provided novel 10-phenyl-1,3,9-triazaanthracenes of the general formula A

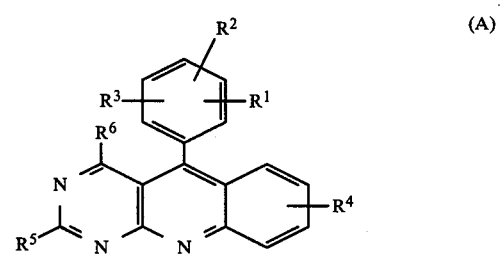

wherein
$R^1$, $R^2$ and $R^3$ are identical or different and each denotes a hydrogen or halogen atom, an alkyl or alkoxy group or a condensed aromatic radical
$R^4$ is a hydrogen or halogen atom, an alkyl, alkoxy, halogenoalkyl, alkylcarbonyl, alkoxycarbonyl or dialkylamino group or a condensed aromatic radical, and
$R^5$ and $R^6$ are identical or different and each denotes hydroxy, alkoxy or dialkylamino groups.

Further objects, features and advantages of the present invention will become apparent from the detailed description of preferred embodiments which follows.

DETAILED DESCRIPTION OF PREFERRED EMBODIMENTS

The novel compounds according to formula (A) can be prepared following the synthesis pathways illustrated below:
In a first step, 2,4,6-trichloro-pyrimidine-5-carbaldehyde (I) is reacted with sulfuryl chloride to form 2,4,6-trichloropyrimidine-5-carboxylic acid chloride (II). The acyl chloride (II) is reacted, by a Friedel-Crafts-reaction, with an appropriately substituted benzene to form a 2,4,6-trichloro-pyrimidine-5-yl-aryl-ketone (III). Compound III is reacted with an aromatic amine in the presence of a tertiary amine to form a 2,4-dichloro-5-aroyl-6-arylamino-pyrimidine (IV).

(IV) can be further reacted in different ways:

By reacting with an alkali metal alcoholate in the corresponding alcohol, a 2-alkoxy-4-chloro-5-aroyl-6-arylamino-pyrimidine (V) is formed.

By reacting (IV) with an excess of a secondary aliphatic amine a 2-dialkylamino-4-chloro-5-aroyl-6-arylamino-pyrimidine (V) is obtained.

When (IV) or (V) is reacted at an elevated temperature either with an alkali metal alcoholate or with an amine, a compound of formula VI is obtained, wherein $R_5$ and $R_6$ are alkoxy or dialkylamino.

Any of the compounds (IV), (V), and (VI) can be cyclized in a concentrated acid to form compound (A).

photopolymerization of vinyl compounds, even in the presence of oxygen. The novel photoinitiators do not initiate thermal polymerization of such compounds when there is no actinic radiation. Therefore, they are very well suited for the preparation of storable copying layers.

It is of advantage that compounds (A) which are essentially free from isomers can be obtained by performing stages (II)→(III) or (III)→(IV), respectively, of the synthesis shown in the preceding diagram in a way such that only one of the possible substitution isomers is predominantly formed. Thus, separating operations are avoided.

The individual reaction steps are simple, safe reactions which in most cases have a high yield. Moreover, the final products of the reactions are compounds not yet described in literature.

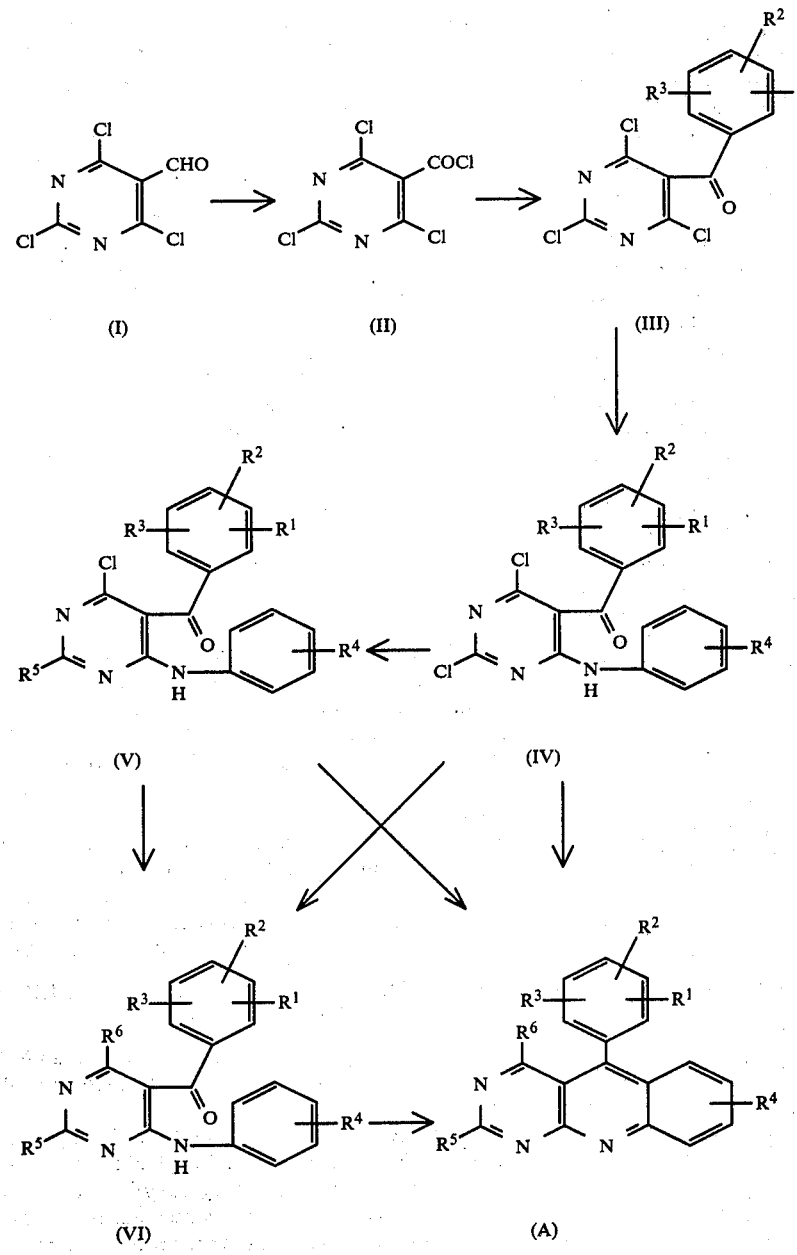

The new compounds absorb light in a spectral range of from about 375 to 430 nm and, when being irradiated in this spectral range, act as active radical starters of the Alkyl and alkoxy groups which can be used as possible substituents in the new compounds of formula (A) generally have 1 to 6, preferably 1 to 3, carbon atoms; methyl and methoxy groups are particularly preferred.

The dialkylamino groups can have 2 to 10, preferably 2 to 6, carbon atoms. The preferred halogen atoms are fluorine and chlorine atoms, and, in the case of $R^4$, particularly fluorine atoms. Preferably used halogenoalkyl groups are those having 1 to 3 carbon atoms, particularly methyl groups, which advantageously are completely halogenated. The same halogen atoms as mentioned above are suitable. In the alkylcarbonyl and alkoxycarbonyl groups, the alkyl and alkoxy groups indicated above can be included. Benzo radicals are especially preferably used as the condensed aromatic radicals.

Of the compounds of the formula (A), particular preference is given to those in which $R^6$ is an —OH or alkoxy group. $R^1$, $R^2$, and $R^3$ are preferably hydrogen or halogen atoms, alkyl, or alkoxy groups or condensed benzo groups. If one of the radicals is a benzo group, the two other radicals preferably are hydrogen atoms. Compounds wherein each of the three radicals $R^1$ to $R^3$ is a hydrogen atom are particularly preferably used.

The added amount of photoinitiators in general varies between 0.01 and 10%, preferably between 0.1 and 5%, by weight, relative to the components of the photopolymerizable layer.

Photopolymerizable monomers useful for the purpose of this invention are known and are, for example, described in U.S. Pat. Nos. 2,760,863 and 3,060,023. Preferred examples are acrylic and methacrylic acid esters, such as diglycerol diacrylate, polyethylene glycol dimethacrylate, acrylates and methacrylates of trimethylol ethane, trimethylol propane, and pentaerythritol and polyhydric alicyclic alcohols. Reaction products of diisocyanates with partial esters of polyhydric alcohols are also used advantageously. Monomers of this kind are described in German Offenlegungsschriften Nos. 20 64 079, 23 61 041 and 28 22 190. The proportion of monomers contained in the layer in general varies between 10 and 80, preferably 20 and 60, percent by weight.

A great number of soluble organic polymers may be employed as binders. Examples are: polyamides, polyvinyl esters, polyvinyl acetals, polyvinyl ethers, epoxide resins, polyacrylic acid esters, polymethacrylic acid esters, polyesters, alkyd resins, polyacrylamide, polyvinyl alcohol, polyethylene oxide, polydimethyl acrylamide, polyvinyl pyrrolidone, polyvinylmethyl formamide, polyvinylmethyl acetamide, and copolymers of the monomers which form the enumerated homopolymers.

Other possible binders are natural substances or modified natural substances, for example, gelatin or cellulose ethers.

With particular advantage, those binders are used which are insoluble in water, but soluble or at least swellable in aqueous-alkaline solutions, since layers containing such binders can be developed with the preferably employed aqueous-alkaline developers. Binders of this type can, for example, contain the following groups: —COOH, —PO$_3$H$_2$, —SO$_3$H, —SO$_2$NH—, or —SO$_2$—NH—CO—. Examples of these are: maleate resins, polymers of β-methacryloyloxy-ethyl N-(p-tolyl-sulfonyl)-carbamate and copolymers of these and similar monomers with other monomers, and also styrene/maleic acid anhydride copolymers. Copolymers of alkylmethacrylates and methacrylic acid and copolymers of methacrylic acid, alkylmethacrylates and methyl methacrylates and/or styrene, acrylonitrile, and the like, which are described in German Offenlegungsschriften Nos. 20 64 080 and 23 63 806, are preferably used.

In general, the added quantity of binder amounts to 20 to 90%, preferably 40 to 80%, by weight of the layer constituents.

Depending on their intended use and desired properties, the photopolymerizable mixtures may contain various additional substances. Examples of these admixtures are:

inhibitors to prevent thermal polymerization of the monomers,
  hydrogen donors,
  substances regulating the sensitomeric
  properties of layers of this type,
  dyes,
  colored and uncolored pigments,
  color formers,
  indicators,
  plasticizers, etc.

These constituents advantageously should be selected to minimize absorption in the range of actinic radiation, which is important for the initiation process.

Within the scope of this invention, actinic radiation is to be understood as any radiation, the energy of which corresponds at least to that of shortwave visible light. Longwave UV-radiation, as well as electron radiation, X-rays, and laser radiation, is suitable.

The photopolymerizable mixture of this invention can be used in many fields of application, such as the production, for example, of safety glass, varnishes which are hardened by the action of light or corpuscular radiation, such as electron beams, and dental fillings, and, in particular, as a light-sensitive copying material in the field of reproduction.

The detailed description of preferred embodiments of the invention is directed to this last field of application, but without the invention being limited thereto. Examples of possible applications in this field are: copying layers for the photomechanical production of printing forms suitable for relief printing, lithographic printing, gravure printing, or screen printing; relief copies, for example, in the production of Braille books; single copies; tanned images; pigment images; etc. The mixtures may further be employed for the photomechanical production of etch resists, for example, for name plates, printed circuits, and chemical milling. The mixtures of this invention are of particular importance with regard to the photomechanical production of lithographic printing forms and etch resists, especially in the form of presensitized materials.

The mixture can be used industrially for the above mentioned applications as a liquid solution or dispersion, for example, a photoresist solution, which is applied by the consumer to an appropriate support, for example, for chemical milling, for the production of printed circuits, screen printing stencils, etc. The mixture may also be present as a solid light-sensitive layer on a suitable support, i.e., as a storable, presensitized copying material, for example, for the production of printing forms. It can also be employed for the production of dry resists.

It is in general advantageous to substantially isolate the mixtures from the influence of atmospheric oxygen during the light polymerization. If the mixture is used in the form of thin copying layers, it is recommended to apply a suitable cover film which has a low permeability to oxygen. The cover film may be self-supporting and be removed from the copying layer prior to development. Polyester films, for example, are suitable for this purpose. The cover film may also consist of a material which dissolves in the developer liquid or which can be removed at least from the non-hardened areas during development. Examples of materials suitable for this purpose are, inter alia, waxes, polyvinyl alcohol, polyphosphates, sugars, etc.

Layer supports which are suitable for copying materials prepared using the mixture of this invention include, for example, aluminum, steel, zinc, copper, plastic films, such as films of polyethylene terephthalate or cellulose acetate, and screen printing supports, such as perlon gauze.

The light-sensitive materials employing the mixture of this invention are conventionally prepared. Thus, the mixture can be taken up in a solvent, and the resulting solution or dispersion can be applied to the intended support as a thin film by casting, spraying, immersion, or roller application and subsequently dried. Thick layers (for example, of 250 μm and thicker) are advantageously prepared by first producing a self-supporting film by extrusion or molding, which is then laminated to the support. In the case of dry resists, solutions of the mixture are applied to transparent intermediate supports and dried. The light-sensitive layers, having a thickness between about 10 and 100 μm, are then also bonded to the desired support by lamination, along with the temporary support.

The copying materials can be processed using known methods. They are developed by treatment with an appropriate developer solution, preferably a weakly alkaline solution, whereby the unexposed areas of the layer are dissolved away and the exposed areas of the copying layer remain on the support.

The following text gives examples of the mixture of the present invention. First, the production of a number of novel photoinitiators according to the invention is described. Since the final stage of the cyclization, which results in compound (A), can be started from three different intermediate products, designated (IV), (V), and (VI) in the preceding reaction schemes, a broad variety of embodiments is possible.

In the production formulations and the Examples which follow, parts by weight (p.b.w.) and parts by volume (p.b.v.) bear the same relationship as the g and the cm$^3$ to one another. Unless otherwise stated, percentages and quantities are to be understood as weight units.

Procedure used for producing compound (II) (2,4,6-trichloropyrimidine-5-carboxylic acid chloride)

At a temperature of 77° C., 0.2 g of azobisisobutyronitrile (AIBN) and 2 moles of sulfuryl chloride are added to a solution of 2 moles of 2,4,6-trichloropyrimidine-5-carbaldehyde in 2 l of tetrachloromethane, and the mixture is kept boiling for 15 hours, during which time 16 ml of sulfuryl chloride and 0.1 g of AIBN are added every 3 hours. After cooling down and filtering, the solvent is removed in vacuo and the residue is distilled. 391.4 g of a colorless distillate (71°–73° C./0.2 mbar) having a melting point of 44° C. are obtained, this yield corresponding to 79.6% of the theoretical of compound (II).

General procedure used for producing the compounds of formula (III)

1 mole of acyl chloride (II) is reacted with 5 to 7 moles of the corresponding aromatic compound $C_6H_5R^1R^2R^3$ and 1.2 moles of aluminum chloride, the solvent used being either an excess of aromatic compound of one of the solvents commonly used for Friedel-Crafts acylations. The reaction mixture is hydrolyzed with HCl/ice, the aqueous phase is extracted as completely as possible by means of an appropriate solvent, and the extraction residue which is left after distilling off of the solvent is recrystallized.

TABLE I

| Compound No. | $R^1$ | $R^2$ | $R^3$ | Melting Point (°C.) | Yield (%) |
|---|---|---|---|---|---|
| III a | H | H | H | 148 | 78.5 |
| b | 4-Cl | H | H | 173 | 81.2 |
| c | 4-CH$_3$ | H | H | 138 | 59.1 |
| d | 2-CH$_3$ | 4-CH$_3$ | H | 128 | 73.3 |
| e | 2-CH$_3$ | 5-CH$_3$ | H | 165 | 83.7 |
| f | 2-CH$_3$ | 4-CH$_3$ | 6-CH$_3$ | 164 | 88.3 |
| g | 4-OCH$_3$ | H | H | 152 | 42.0 |
| h | 2,3-benzo | | H | 197 | 62.9 |

General procedure used for producing the compounds of general formula (IV)

1 mole of (III) is reacted with 1 mole of an aromatic amine and 1.1 moles of a tertiary amine, preferably triethylamine, in a solvent which is inert under the reaction conditions, preferably tetrahydrofuran, dioxane, or a dialkylether, at a temperature of between 0° and 40° C., preferably 20° C. The triethylamine hydrochloride is filtered off, the solvent is removed by distillation, and the residue thus obtained is crystallized by mixing with an appropriate solvent.

TABLE II

| | $R^2 = R^3 = H$ | | | |
|---|---|---|---|---|
| Compound No. | $R^1$ | $R^4$ | Melting Point (°C.) | Yield (%) |
| IV a | H | H | 128 | 76.4 |
| b | H | 2-OCH$_3$ | 132 | 67.4 |
| c | H | 4-OCH$_3$ | 86 | 40.1 |
| d | H | 4-F | 163 | 69.0 |
| e | H | 4-CO$_2$CH$_3$ | 182 | 42.7 |
| f | H | 4-CF$_3$ | 183 | 33.5 |
| g | 4-Cl | 4-Cl | 177 | 81.3 |
| h | 4-Cl | 2-OCH$_3$ | 162 | 59.2 |
| i | H | 4-N(C$_2$H$_5$)$_2$ | 148 | 55.4 |
| j | H | 4-COCH$_3$ | 150 | 44.0 |
| k | H | 3,4-benzo | 142 | 73.6 |

General procedure used for producing the compounds of general formula (V)

0.1 mole of (IV) is either reacted at room temperature with 0.1 mole of alkali metal alcoholate MeR$^5$ in the corresponding alcohol, for a period of 5 hours, whereupon the solids are filtered off by suction, washed with alcohol and water and dried; or is reacted at room temperature with 0.3 mole of amine R$^5$H in tetrahydrofuran for 1 to 5 hours while stirring, whereupon the reaction mixture is filtered off from the amine hydrochloride and, after removal of the solvent, the filtrate is crystallized by stirring with an appropriate solvent.

TABLE III $R^2 = R^3 = H$

| Compound No. | $R^1$ | $R^4$ | $R^5$ | $R^6$ | Melting Point (°C.) | Yield (%) |
|---|---|---|---|---|---|---|
| V a | H | H | $OCH_3$ | Cl | 122 | 78.2 |
| b | H | H | $N(C_2H_5)_2$ | Cl | 137 | 49.9 |
| c | H | 4-F | $N(C_2H_5)_2$ | Cl | 104 | 85.3 |
| d | H | 4-$CF_3$ | $N(C_2H_5)_2$ | Cl | 131 | 80.7 |
| e | H | 4-$CO_2CH_3$ | $N(C_2H_5)_2$ | Cl | 131 | 86.5 |
| f | H | 4-$COCH_3$ | $N(C_2H_5)_2$ | Cl | 144 | 66.6 |
| g | H | 4-$OCH_3$ | $N(C_2H_5)_2$ | Cl | 88 | 86.3 |

General procedure used for producing the compounds of general formula (VI)

In order to introduce substituents into the 2- and/or 4-position of the pyrimidine ring, 0.1 mole of (IV) or (V) is either heated to 70° for 10 to 15 hours with 0.4 mole of alkali metal alcoholate in the corresponding alcohol, the solids are filtered off by suction after cooling down, washed with alcohol and water and recrystallized; or 0.1 mole of (IV) or (V) is heated to a boil for 12 to 16 hours with 0.5 mole of amine in tetrahydrofuran or acetonitrile, the amine hydrochloride is separated off by filtration, and the filtrate left after removal of the solvent is crystallized by stirring with an appropriate solvent.

TABLE IV $R^2 = R^3 = H$

| compound No. | $R^1$ | $R^4$ | $R^5$ | $R^6$ | Melting Point °C. | Yield (%) |
|---|---|---|---|---|---|---|
| VI a | H | H | $OCH_3$ | $OCH_3$ | 140 | 87.2 |
| b | H | H | $N(C_2H_5)_2$ | $OCH_3$ | 106 | 86.3 |
| c | H | 2-$OCH_3$ | $OCH_3$ | $OCH_3$ | 183 | 84.3 |
| d | H | 4-F | $OCH_3$ | $OCH_3$ | 146 | 92.0 |
| e | H | 4-$CO_2CH_3$ | $N(C_2H_5)_2$ | $OCH_3$ | 142 | 58.2 |
| f | H | 4-$CO_2CH_3$ | $OCH_3$ | $OCH_3$ | 138 | 70.4 |
| g | H | 4-$CF_3$ | $N(C_2H_5)_2$ | $OCH_3$ | 124 | 81.7 |
| h | H | 4-$CF_3$ | $OCH_3$ | $OCH_3$ | 142 | 76.5 |
| i | 4-Cl | 4-Cl | $OCH_3$ | $OCH_3$ | 181 | 88.6 |
| j | 4-Cl | 2-$OCH_3$ | $OCH_3$ | $OCH_3$ | 135 | 89.9 |
| k | H | 4-$OCH_3$ | $OCH_3$ | $OCH_3$ | 137 | 93.3 |
| l | H | 4-$OCH_3$ | $N(C_2H_5)_2$ | $OCH_3$ | 95 | 75.8 |
| m | H | 4-F | $N(C_2H_5)_2$ | $OCH_3$ | 86 | 91.8 |
| n | H | 4-$N(C_2H_5)_2$ | $OCH_3$ | $OCH_3$ | 109 | 88.2 |
| o | H | 4-$CO_2CH_3$ | $N(C_2H_5)_2$ | $N(C_2H_5)_2$ | 124 | 74.0 |
| p | H | 4-$COCH_3$ | $N(C_2H_5)_2$ | $OCH_3$ | 148 | 85.8 |
| q | H | 4-$COCH_3$ | $OCH_3$ | $OCH_3$ | 138 | 74.3 |
| r | H | 3,4-benzo | $OCH_3$ | $OCH_3$ | 123 | 83.6 |

General procedure used for producing the compounds of general formula (A)

At a temperature of 40° to 50° C., 1 p.b.w. of (IV), (V) or (VI) is added to a mixture of 10 p.b.v. of trifluoroacetic acid and 1 p.b.v. of sulphuric acid (98%) and stirred until the reaction is completed while maintaining the same temperature. The reaction product is then poured on 50 p.b.v. of ice and adjusted to a pH of 8 by means of an alkaline compound, and the solids are separated off, washed in a neutral medium, and recrystallized from dimethylformamide. During the reaction, cyclization into a pyridine ring takes place. If (IV) or (V) is employed, the chlorine atoms $R^5$ and/or $R^6$ are at the same time replaced by OH groups.

TABLE V $R^2 = R^3 = H$

| compound No. | $R^1$ | $R^4$ | $R^5$ | $R^6$ | Melting Point °C. | Yield % |
|---|---|---|---|---|---|---|
| A a | H | H | OH | OH | 350 | 81.9 |
| b | H | H | $OCH_3$ | $OCH_3$ | 207 | 55.1 |
| c | H | H | $OCH_3$ | OH | 250 | 85.2 |
| d | H | H | $N(C_2H_5)_2$ | OH | 329 | 66.4 |
| e | H | H | $N(C_2H_5)_2$ | $OCH_3$ | 199 | 50.4 |
| f | H | 9-$OCH_3$ | $OCH_3$ | $OCH_3$ | 208 | 72.6 |
| g | H | 7-$OCH_3$ | $N(C_2H_5)_2$ | OH | 288 | 48.4 |
| h | H | 7-F | $N(C_2H_5)_2$ | OH | 330 | 35.0 |
| i | H | 7-F | $OCH_3$ | $OCH_3$ | 210 | 15.8 |
| j | H | 7-$CO_2CH_3$ | $N(C_2H_5)_2$ | OH | 259 | 56.7 |
| k | H | 7-$CO_2CH_3$ | $N(C_2H_5)_2$ | $OCH_3$ | 224 | 33.3 |
| l | H | 7-$CO_2CH_3$ | $OCH_3$ | $OCH_3$ | 268 | 47.2 |
| m | H | 7-$CF_3$ | $N(C_2H_5)_2$ | OH | 237 | 14.3 |
| n | H | 7-$CF_3$ | $N(C_2H_5)_2$ | $OCH_3$ | 199 | 5.7 |
| o | H | 7-$CF_3$ | $OCH_3$ | $OCH_3$ | 221 | 37.5 |
| p | 4-Cl | 7-Cl | OH | OH | 350 | 75.2 |
| q | 4-Cl | 7-Cl | $OCH_3$ | $OCH_3$ | 244 | 41.9 |
| r | 4-Cl | 9-$OCH_3$ | $OCH_3$ | $OCH_3$ | 248 | 73.3 |

The initiating activity of all initiators according to formula A a-r is shown by tables in a number of Examples.

EXAMPLE 1

A solution of
4.0 p.b.w. of a methylmethacrylate/methacrylic acid copolymer (acid number about 110)
4.0 p.b.w. of trimethylolethanetriacrylate,
0.08 p.b.w. of a blue azo dyestuff obtained by coupling 2,4-dinitro-6-chlorobenzene diazonium salt with 2-methoxy-5-acetylamino-N-cyanoethyl-N-hydroxyethylaniline, and
0.21 p.b.w. of initiator, in
38 p.b.w. of ethyleneglycol monoethyl ether and
18 p.b.w. of butyl acetate
is spin-coated onto electrolytically roughened and anodically oxidized, 0.3 mm thick aluminum and dried, in a way such that a dry layer weight of 25 g/m² is obtained.

After drying, the photopolymer layer is provided with a coating comprised of a solution of
5 p.b.w. of polyvinyl alcohol (12% residual acetyl groups, K-value 8), in
95 p.b.w. of purified water
and dried, so that a peelable cover layer having a weight of about 5 g/m² is obtained.

Subsequently, the plate is exposed for 40 seconds by means of a 5 kW metal halide lamp, through a 13-step exposure wedge. After exposure, the plate is heated to 90° C. for a short time. Then the exposed photopolymer layer is developed for about 1 minute with a developer of
1.5 p.b.w. of sodium metasilicate $\times 9H_2O$
0.01 p.b.w. of a polyoxyethylene ether of coconut fatty alcohol having about 8 oxyethylene units, and
98.3 p.b.w. of purified water,
using a cotton pad.

The plate is rinsed with water and rendered acidic with 1% strength phosphoric acid and inked with a greasy ink.

After inking, the plate is treated with a commercially available desentisizing gumming solution and dried. On an offset press about 100,000 prints can be run.

The following light sensitivities are measured:

| Compound | Developed solid steps |
| --- | --- |
| A a | 2 |
| b | 1 |
| c | 1 |
| d | 3 |
| e | 2 |
| f | 2 |
| g | 4 |
| h | 2 |
| i | 5 |
| j | 3 |
| k | 3 |
| l | 5 |
| m | 4 |
| n | 3 |
| o | 5 |
| p | 2 |
| q | 1 |
| r | 2 |

EXAMPLE 2

4 solutions, which are each composed of
5.6 p.b.w. of the product obtained by reacting 1 mole of 2,4,4-trimethyl-hexamethylene diisocyanate with 2 moles of 2-hydroxy-ethyl methacrylate,
6.5 p.b.w. of a terpolymer of styrene, n-hexylmethacrylate and methacrylic acid (10:60:30),
0.2 p.b.w. of one of the compounds Ai, Al, Am and Ao,
0.15 p.b.w. of triethylene glycol dimethacrylate, and
0.035 p.b.w. of the blue azo dyestuff described in Example 1, in
30 p.b.w. of butanone and
0.5 p.b.w. of ethyl alcohol
are successively spin-coated onto 25 μm thick polyethylene terephthalate film, in a way such that a 25 μm thick layer (30 g/m²) is obtained. Then the plates are dried in a drying cabinet at 100° C. for 2 minutes.

In order to protect the layers thus produced from contamination by dust or damage, they are covered with a cover film having a thickness of 20–25 μm, whereby the adhesion between the cover film and the light-sensitive layer is smaller than the adhesion between the layer and the polyester support. Thus treated, the plates can be stored over a relatively long period of time.

The copper surface of a phenoplast laminate plate, to which a 35 μm thick copper foil is bonded, is mechanically cleaned with pumice powder or a brushing machine and blown dry with oil-free air after thorough rinsing with water.

The cover film is peeled off, and the dry resist is laminated onto the cleaned copper plates by means of a laminating device equipped with heated rolls, at a temperature of 120° C. and a speed of 1.5 m/min.

Then the four samples are exposed through the support film, under a 13-step exposure wedge having density increments of 0.15. Exposure is performed by means of a 5 kW metal halide lamp, the exposure times are 10, 20, and 40 seconds.

The wedge step 0 corresponds to an optical density of 0.05 (auto-absorption of the film material).

After removal of the support film, the plates are spray-developed with an 0.8% sodium carbonate solution. The developing time is about 60 seconds at a temperature of 23° C.

In order to test the developer resistance—it is the purpose of this test to find out whether the wedge steps are completely cross-linked—the samples are subjected to the threefold developing time, i.e., 180 seconds, after exposure for 20 seconds.

In the following table, the completely cross-linked wedge steps of the dry resist layers are compiled, the layers differing from one another merely by the photoinitiator used in each case:

| Compound | Solid steps in the sprayer at | | | Solid steps after 180 sec development |
| --- | --- | --- | --- | --- |
| | 10 sec | 20 sec exposure | 40 sec | |
| A i | 2 | 4 | 6 | 3 |
| l | 1 | 3 | 5 | 2 |
| m | 2 | 4 | 6 | 3 |
| o | 1 | 3 | 4 | 2 |

EXAMPLE 3

0.4 g each of the compounds Ai, Al, Am and Ao are added to photopolymer mixtures, as described in Example 2, and the solutions are spin-coated onto 25 μm thick polyethylene terephthalate films, in a way such that 25 μm thick layers (30 g/m²) are obtained.

Following the procedure of Example 2, the layers are then applied to the cleaned copper surfaces of 10 cm × 15 cm Cu-Pertinax plates, exposed through the support film, and developed with an 8% aqueous sodium carbonate solution.

The following numbers of completely crosslinked wedge steps result (comparison: number of solid steps when each solution contains 0.6 g of initiator):

| Compound | Solid steps with 0,4 g of initiator Exposure time (sec) | | | Comparison: Solid steps with 0.6 g of initiator Exposure time (sec) | | |
| --- | --- | --- | --- | --- | --- | --- |
| | 10 | 20 | 40 | 10 | 20 | 40 |
| A i | 4 | 6 | 8 | 3 | 5 | 7 |
| l | 3 | 5 | 7 | 2 | 4 | 6 |
| m | 4 | 6 | 8 | 2 | 4 | 7 |
| o | 2 | 4 | 6 | 1 | 3 | 5 |

EXAMPLE 4

A solution of
1.0 p.b.w. trimethylolethane triacrylate,
1.4 p.b.w. of a terpolymer comprised of n-hexyl methacrylate, methyl methacrylate and methacrylic acid (50:25:25) and having an acid numer of about 160,
0.02 p.b.w. of Sudan Blue II, and
0.05 p.b.w. of compound Ai, in
6.0 p.b.w. of butanone
is spin-coated onto a cleaned single-stage zinc etch plate and dried, in a way such that a layer weight of about 10 g/m² is obtained.

Thereafter, the copying material is provided with a 1–2 μm thick coating of polyvinyl alcohol, dried and exposed for 40 seconds under a positive original using a 5 kW metal halide lamp. The zinc plate is developed for 45 seconds with a developer composed of
1.5 p.b.w. of sodium metasilicate nonahydrate
0.3 p.b.w. of polyglycol 6,000
0.3 p.b.w. of levulinic acid
0.3 p.b.w. of strontium hydroxide × 8H₂O, and
97.6 p.b.w. of purified water.

After thorough rinsing with water, etching is performed for 5 minutes with 10% strength nitric acid containing an edge protecting agent. The hardened photopolymer layer is removed with ethyleneglycol monobutyl ether. The printing form obtained can be used for high quality book printing.

EXAMPLE 5

A coating solution as described in Example 4, but containing 0.05 p.b.w. of compound Am instead of compound Ai is applied by casting to a 25 μm thick polyethylene terephthalate film, in a way such that a 20 μm thick layer (26 g/m²) is obtained. Then drying is performed at 100° C. in a drying cabinet for 2 minutes.

Together with the polyester film, the dried layer is laminated onto a screen printing cloth VS Monoprint P 77 made by Verseidag, Krefeld, by means of a laminating device employing the highest possible pressure, a temperature of 115° C., and a speed of 1 m/min.

Thereafter, exposure is performed under a positive original for 60 seconds through the polyester film, by means of a 5 kW metal halide lamp.

The polyester film is removed and the non-crosslinked image areas are removed with the developer described in Example 4 in a swing bath within 45 seconds. After thorough rinsing with water and drying, the screen printing form is ready for use.

What is claimed is:

1. A photopolymerizable mixture consisting essentially of:
   (a) a polymeric binder,
   (b) a polymerizable compound having at least two terminal ethylenically unsaturated groups and a boiling point of more than 100° C., and
   (c) a polynuclear N-hetercyclic compound of the formula A as a photoinitiator

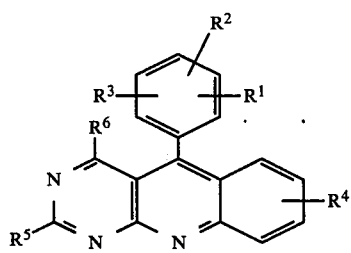

(A)

wherein
$R^1$, $R^2$ and $R^3$ are identical or different and each denotes a hydrogen or halogen atom, an alkyl or alkoxy group or a condensed aromatic radical,
$R^4$ is a hydrogen or halogen atom, an alkyl, alkoxy, halogenoalkyl, alkylcarbonyl, alkoxycarbonyl or dialkylamino group or a condensed aromatic radical, and
$R^5$ and $R^6$ are identical or different and denote hydroxy, alkoxy or dialkylamino groups.

2. A photopolymerizable mixture as in claim 1, wherein $R^1$, $R^2$ and $R^3$ are hydrogen atoms.

3. A photopolymerizable mixture as in claim 1, wherein $R^6$ is a hydroxy group or an alkoxy group.

4. A photopolymerizable mixture as in claim 1, wherein said alkyl and alkoxy groups of $R^1$, $R^2$, $R^3$, $R^4$, $R^5$, and $R^6$ have 1 to 3 carbon atoms.

5. A photopolymerizable mixture as in claim 1, wherein said dialkylamino groups of $R^4$, $R^5$, and $R^6$ have 2 to 6 carbon atoms.

6. A photopolymerizable mixture as in claim 1, wherein $R^4$ is a fluorine atom.

7. A photopolymerizable mixture as in claim 1, wherein said halogenoalkyl group of $R^4$ has 1 to 3 carbon atoms that are completely halogenated.

8. A photopolymerizable mixture as in claim 1, wherein said condensed aromatic radicals of $R^1$, $R^2$, $R^3$, and $R^4$ are benzo radicals.

9. A photopolymerizable mixture as in claim 1, wherein one of $R^1$, $R^2$, and $R^3$ is a benzo group and the other radicals are both hydrogen atoms.

10. A photopolymerizable mixture as in claim 1, wherein said polymeric binder is soluble or swellable in aqueous alkaline solutions.

11. A photopolymerizable mixture as in claim 10, wherein said polymeric binder is a copolymer selected from the group consisting of copolymers of alkylmethacrylates, methyl methacrylate, methacrylic acid and/or styrene.

12. A compound of the formula

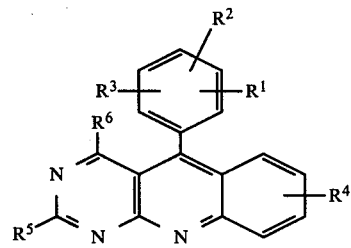

wherein
$R^1$, $R^2$ and $R^3$ are identical or different and each denotes a hydrogen or halogen atom, an alkyl or alkoxy group or a condensed aromatic radical,
$R^4$ is a hydrogen or halogen atom, an alkyl, alkoxy, halogenoalkyl, alkylcarbonyl, alkoxycarbonyl or dialkylamino group or a condensed aromatic radical, and
$R^5$ and $R^6$ are identical or different and denote hydroxy, alkoxy or dialkylamino groups.

13. A compound as in claim 12, wherein said alkyl and alkoxy groups of $R^1$, $R^2$, $R^3$, $R^4$, $R^5$, and $R^6$ have 1 to 3 carbon atoms.

14. A compound as in claim 12, wherein said dialkylamino groups of $R^4$, $R^5$, and $R^6$ have 2 to 6 carbon atoms.

15. A compound as in claim 12, wherein $R^4$ is a fluorine atom.

16. A compound as in claim 12, wherein said halogenoalkyl group of $R^4$ has 1 to 3 carbon atoms that are completely halogenated.

17. A compound as in claim 12, wherein said condensed aromatic radicals of $R^1$, $R^2$, $R^3$, and $R^4$ are benzo radicals.

18. A compound as in claim 12, wherein one of $R^1$, $R^2$, and $R^3$ is a benzo group and the other radicals are both hydrogen atoms.

* * * * *